US007128726B2

(12) United States Patent
Crawford et al.

(10) Patent No.: US 7,128,726 B2
(45) Date of Patent: *Oct. 31, 2006

(54) SAFETY NEEDLE ASSEMBLY

(75) Inventors: Jamieson W. M. Crawford, New York, NY (US); Michael Bennett, Summit, NJ (US); C. Mark Newby, Tuxedo, NY (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 295 days.

This patent is subject to a terminal disclaimer.

(21) Appl. No.: 10/771,726

(22) Filed: Feb. 4, 2004

(65) Prior Publication Data

US 2004/0186439 A1 Sep. 23, 2004

Related U.S. Application Data

(63) Continuation of application No. 10/170,318, filed on Jun. 12, 2002, now Pat. No. 6,699,217.

(51) Int. Cl.
A61M 5/00 (2006.01)
A61M 5/32 (2006.01)

(52) U.S. Cl. .................. 604/110; 604/192; 128/919

(58) Field of Classification Search ............... 604/110, 604/187, 192, 198, 263; 128/919
See application file for complete search history.

(56) References Cited

U.S. PATENT DOCUMENTS

| 1,779,451 A | 10/1930 | Sponsel |
|---|---|---|
| 2,004,050 A | 6/1935 | Kerk |
| 2,700,385 A | 1/1955 | Ortiz |
| 2,836,942 A | 6/1958 | Miskel |
| 2,854,976 A | 10/1958 | Heydrich |
| 2,953,243 A | 9/1960 | Roeher |
| 3,021,942 A | 2/1962 | Hamilton |
| 3,073,307 A | 1/1963 | Stevens |
| 3,074,542 A | 1/1963 | Myerson et al. |
| 3,255,873 A | 6/1966 | Speelman |
| 3,294,231 A | 12/1966 | Vanderbeck |
| 3,323,523 A | 6/1967 | Scislowicz et al. |
| 3,329,146 A | 7/1967 | Waldman, Jr. |
| 3,333,682 A | 8/1967 | Burke |
| 3,367,488 A | 2/1968 | Hamilton |
| 3,485,239 A | 12/1969 | Vanderbeck |
| 3,537,452 A | 11/1970 | Wilks |
| 3,610,240 A | 10/1971 | Harautuneian |
| 3,658,061 A | 4/1972 | Hall |
| 3,828,775 A | 8/1974 | Armel |
| 3,890,971 A | 6/1975 | Leeson et al. |
| 3,904,033 A | 9/1975 | Haerr |
| 3,934,722 A | 1/1976 | Goldberg |
| 3,968,876 A | 7/1976 | Brookfield |
| 4,113,090 A | 9/1978 | Carstens |

(Continued)

FOREIGN PATENT DOCUMENTS

GB    1 233 302    5/1971

(Continued)

*Primary Examiner*—LoAn H. Thanh
(74) *Attorney, Agent, or Firm*—Mark Lindsey

(57) ABSTRACT

The present invention is a safety shield assembly having a shield and a collar for connecting the shield to a fluid handling device whereby the shield may be pivoted with respect to the collar. Preferably, the safety shield assembly may be used with a needle assembly, an intravenous infusion set a syringe, a catheter or other fluid handling devices or assemblies that contain piercing elements. The shield includes a clip with a plurality of cannula finger locks for preventing re-exposure of the used needle.

15 Claims, 17 Drawing Sheets

U.S. PATENT DOCUMENTS

| | | |
|---|---|---|
| 4,139,009 A | 2/1979 | Alvarez |
| 4,175,008 A | 11/1979 | White |
| 4,300,678 A | 11/1981 | Gyure et al. |
| RE31,086 E | 11/1982 | Johnson, Jr. et al. |
| 4,375,849 A | 3/1983 | Hanifl |
| 4,430,082 A | 2/1984 | Schwabacher |
| 4,592,744 A | 6/1986 | Jagger et al. |
| 4,634,428 A | 1/1987 | Cuu |
| 4,643,722 A | 2/1987 | Smith, Jr. |
| 4,659,330 A | 4/1987 | Nelson et al. |
| 4,664,249 A | 5/1987 | Gheradi |
| 4,664,259 A | 5/1987 | Landis |
| 4,664,654 A | 5/1987 | Strauss |
| 4,671,408 A | 6/1987 | Raines et al. |
| 4,681,567 A | 7/1987 | Masters et al. |
| 4,695,274 A | 9/1987 | Fox |
| 4,702,738 A | 10/1987 | Spencer |
| 4,723,943 A | 2/1988 | Spencer |
| 4,728,320 A | 3/1988 | Chen |
| 4,728,321 A | 3/1988 | Chen |
| 4,731,059 A | 3/1988 | Wanderer et al. |
| 4,735,311 A | 4/1988 | Lowe et al. |
| 4,735,618 A | 4/1988 | Hagen |
| 4,737,144 A | 4/1988 | Choksi |
| 4,738,663 A | 4/1988 | Bogan |
| 4,743,233 A | 5/1988 | Schneider |
| 4,746,008 A | 5/1988 | Heverly et al. |
| 4,747,836 A | 5/1988 | Luther |
| 4,747,837 A | 5/1988 | Hauck |
| 4,772,272 A | 9/1988 | McFarland |
| 4,778,453 A | 10/1988 | Lopez |
| 4,781,697 A | 11/1988 | Slaughter |
| 4,782,841 A | 11/1988 | Lopez |
| 4,790,828 A | 12/1988 | Dombrowski et al. |
| 4,793,484 A | 12/1988 | Schoettle |
| 4,795,432 A | 1/1989 | Karczmer |
| 4,795,443 A | 1/1989 | Permenter et al. |
| 4,801,295 A | 1/1989 | Spencer |
| 4,804,372 A | 2/1989 | Laico et al. |
| 4,813,426 A | 3/1989 | Haber et al. |
| 4,816,022 A | 3/1989 | Poncy |
| 4,816,024 A | 3/1989 | Sitar et al. |
| 4,819,659 A | 4/1989 | Sitar |
| 4,820,277 A | 4/1989 | Norelli |
| 4,826,490 A | 5/1989 | Byrne et al. |
| 4,826,491 A | 5/1989 | Schramm |
| 4,838,871 A | 6/1989 | Luther |
| 4,842,587 A | 6/1989 | Poncy |
| 4,846,796 A | 7/1989 | Carrell et al. |
| 4,850,968 A | 7/1989 | Romano |
| 4,850,976 A | 7/1989 | Heinrich et al. |
| 4,850,977 A | 7/1989 | Bayless |
| 4,850,978 A | 7/1989 | Dudar et al. |
| 4,850,994 A | 7/1989 | Zerbst et al. |
| 4,850,996 A | 7/1989 | Cree |
| 4,858,607 A | 8/1989 | Jordan et al. |
| 4,863,434 A | 9/1989 | Bayless |
| 4,863,435 A | 9/1989 | Sturman et al. |
| 4,863,436 A | 9/1989 | Glick |
| 4,867,746 A | 9/1989 | Dufresne |
| 4,872,552 A | 10/1989 | Unger |
| 4,874,383 A | 10/1989 | McNaughton |
| 4,874,384 A | 10/1989 | Nunez |
| 4,883,469 A | 11/1989 | Glazier |
| 4,886,503 A | 12/1989 | Miller |
| 4,888,001 A | 12/1989 | Schoenberg |
| 4,892,107 A | 1/1990 | Haber |
| 4,892,521 A | 1/1990 | Laico et al. |
| 4,900,309 A | 2/1990 | Netherton et al. |
| 4,909,791 A | 3/1990 | Norelli |
| 4,909,792 A | 3/1990 | Norelli |
| 4,921,096 A | 5/1990 | McFarlane |
| 4,927,018 A | 5/1990 | Yang et al. |
| 4,944,397 A | 7/1990 | Miller |
| 4,966,591 A | 10/1990 | Yuen |
| 4,976,699 A | 12/1990 | Gold |
| 4,982,842 A | 1/1991 | Hollister |
| 5,011,475 A | 4/1991 | Olson |
| 5,011,479 A | 4/1991 | Le et al. |
| 5,055,102 A | 10/1991 | Sitnik |
| 5,078,693 A | 1/1992 | Shine |
| 5,116,325 A | 5/1992 | Paterson |
| 5,135,509 A | 8/1992 | Olliffe |
| 5,139,489 A | 8/1992 | Hollister |
| 5,151,089 A | 9/1992 | Kirk, III et al. |
| 5,154,285 A | 10/1992 | Hollister |
| 5,188,611 A | 2/1993 | Orgain |
| 5,197,954 A | 3/1993 | Cameron |
| 5,207,653 A | 5/1993 | Janjua et al. |
| 5,232,454 A | 8/1993 | Hollister |
| 5,232,455 A | 8/1993 | Hollister |
| 5,242,417 A | 9/1993 | Paudler |
| 5,277,311 A | 1/1994 | Hollister |
| 5,312,369 A | 5/1994 | Arcusin et al. |
| 5,401,251 A | 3/1995 | Hui |
| 5,405,332 A | 4/1995 | Opalek |
| 5,423,765 A | 6/1995 | Hollister |
| 5,462,534 A | 10/1995 | Debreczeni |
| 5,485,854 A | 1/1996 | Hollister |
| 5,486,163 A | 1/1996 | Haynes |
| 5,490,841 A | 2/1996 | Landis |
| 5,509,907 A | 4/1996 | Bevilacqua |
| 5,533,984 A | 7/1996 | Parmigiani |
| 5,584,816 A | 12/1996 | Gyure et al. |
| 5,599,313 A | 2/1997 | Gyure et al. |
| 5,599,318 A | 2/1997 | Sweeney et al. |
| 5,603,699 A | 2/1997 | Shine |
| 5,632,732 A | 5/1997 | Szabo et al. |
| 5,643,219 A | 7/1997 | Burns |
| 5,662,617 A | 9/1997 | Odell et al. |
| 5,665,075 A | 9/1997 | Gyure et al. |
| 5,669,889 A | 9/1997 | Gyure et al. |
| 5,693,022 A | 12/1997 | Haynes |
| 5,702,369 A | 12/1997 | Mercereau |
| 5,733,265 A | 3/1998 | Bachman et al. |
| 5,807,351 A | 9/1998 | Kashmer |
| 5,836,920 A | 11/1998 | Robertson |
| 5,885,249 A | 3/1999 | Irisawa |
| 5,913,846 A | 6/1999 | Szabo |
| 5,993,426 A | 11/1999 | Hollister |
| 6,077,253 A | 6/2000 | Cosme |
| 6,080,137 A | 6/2000 | Pike |
| 6,120,482 A | 9/2000 | Szabo |
| 6,139,533 A | 10/2000 | Xia et al. |
| RE37,110 E | 3/2001 | Hollister |
| RE37,252 E | 7/2001 | Hollister |
| 6,319,232 B1 | 11/2001 | Kashmer |
| 6,328,713 B1 | 12/2001 | Hollister |
| 6,334,857 B1 | 1/2002 | Hollister et al. |

FOREIGN PATENT DOCUMENTS

| | | |
|---|---|---|
| GB | 2 239 604 | 7/1991 |
| GB | 2 239 607 | 7/1991 |
| GB | 2 240 273 | 7/1991 |
| GB | 2 240 477 | 8/1991 |
| WO | WO 87/07162 | 12/1987 |
| WO | WO 90/01348 | 2/1990 |
| WO | WO 91/09637 | 7/1991 |
| WO | WO 91/09638 | 7/1991 |
| WO | WO 91/09639 | 7/1991 |
| WO | WO 93/16745 | 9/1993 |

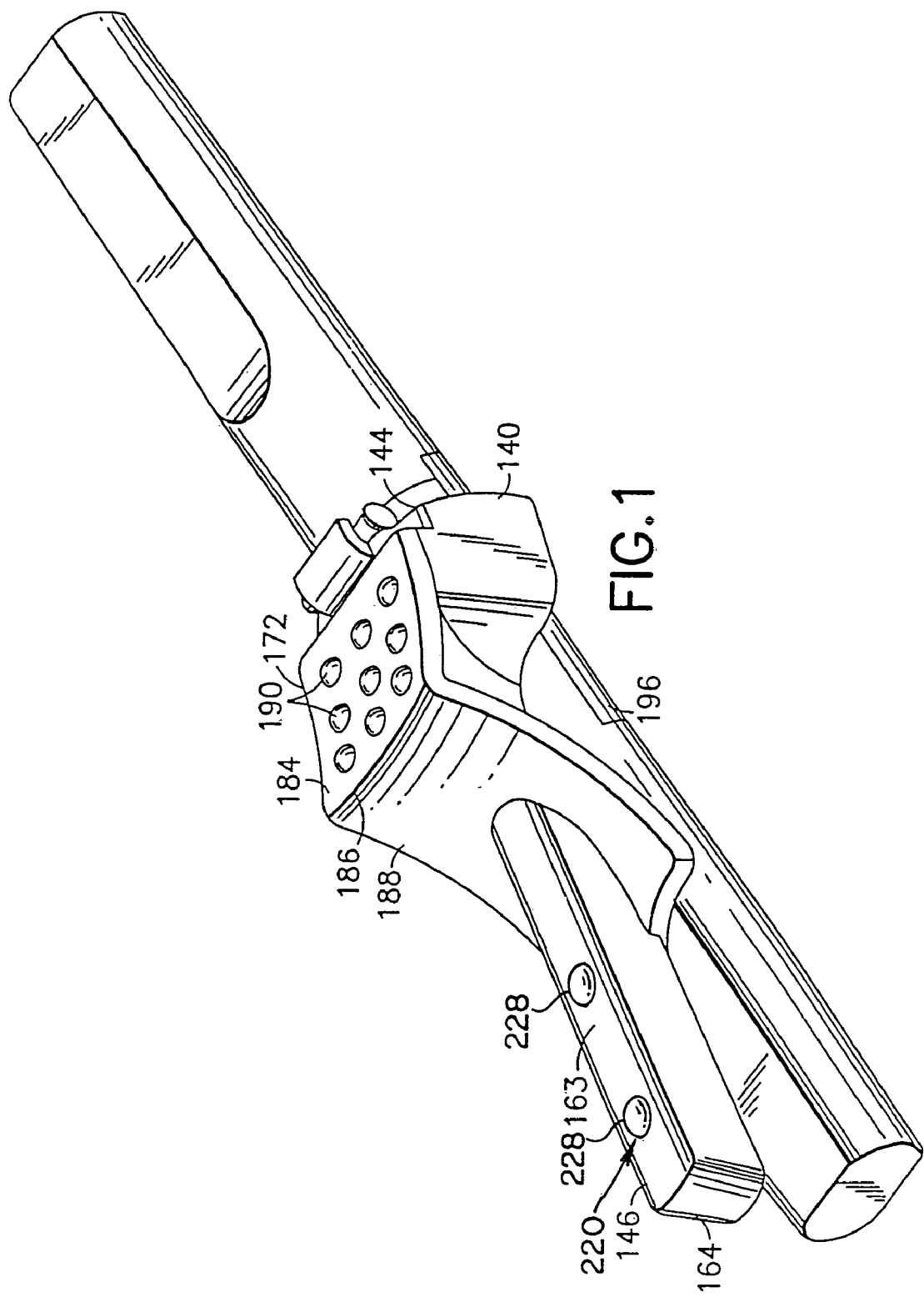

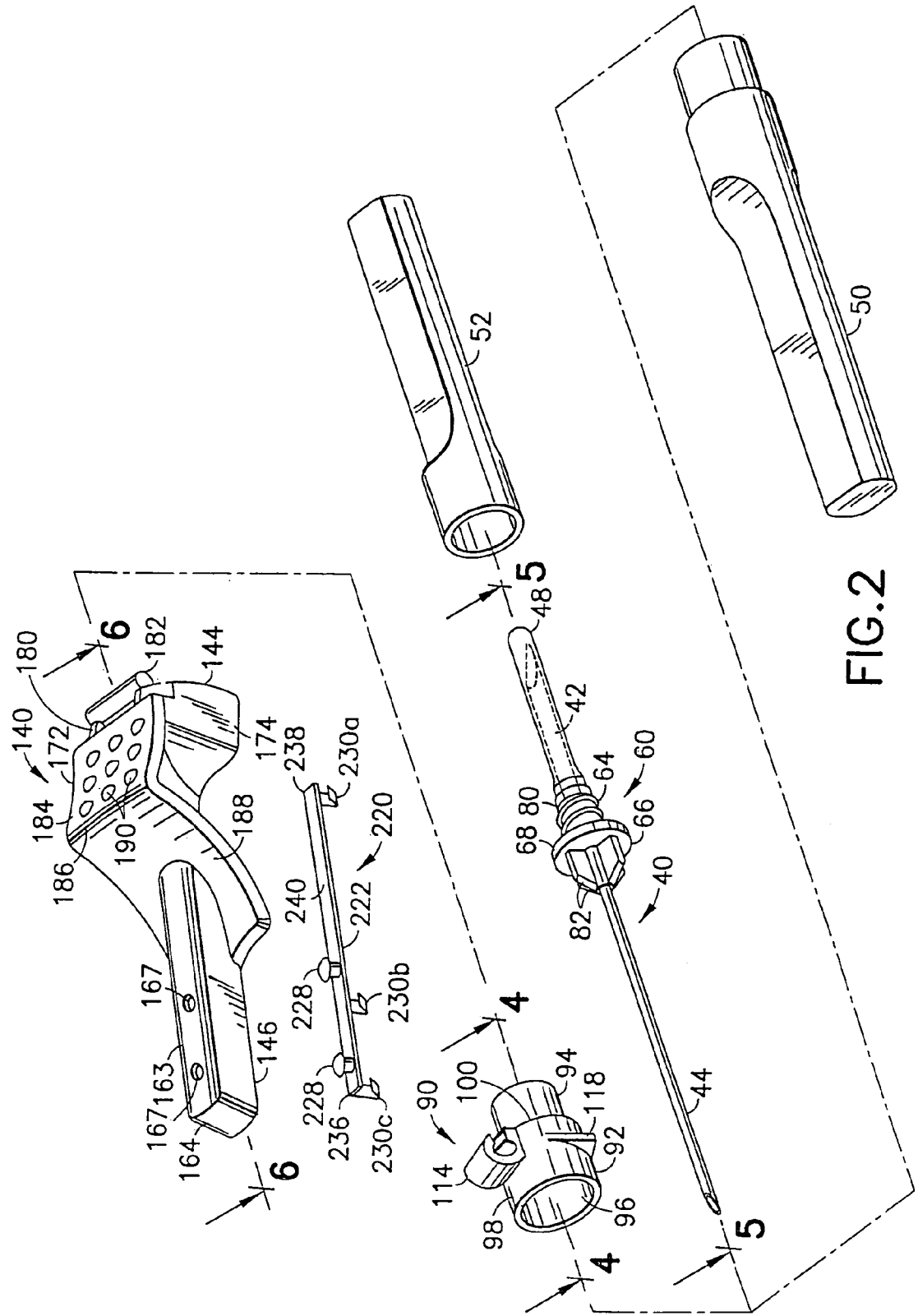

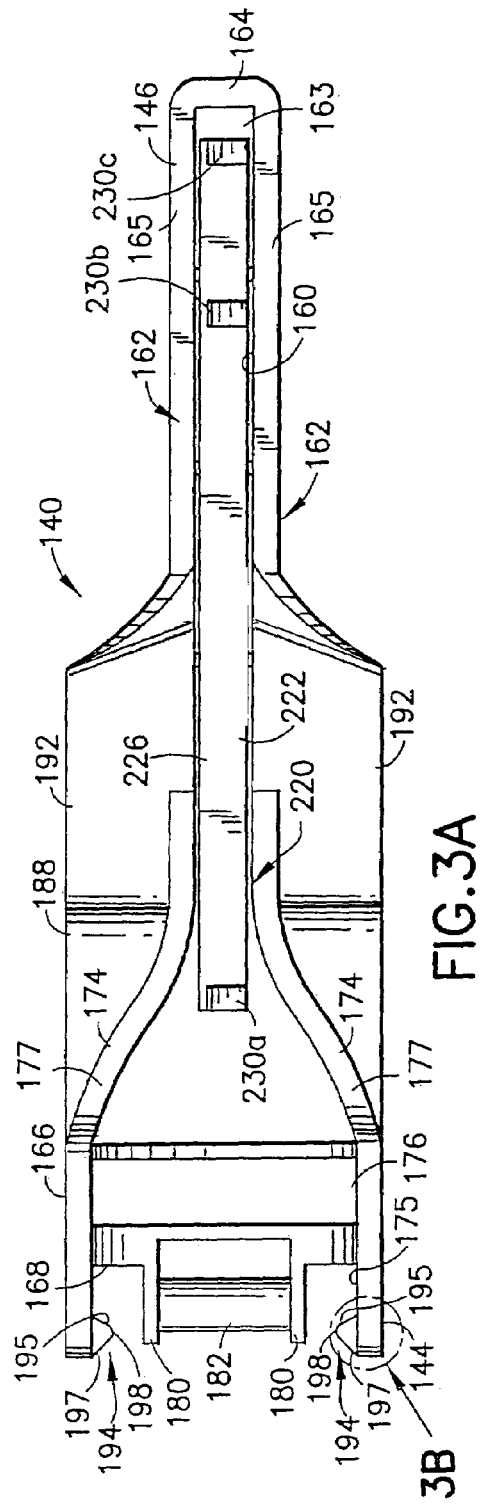

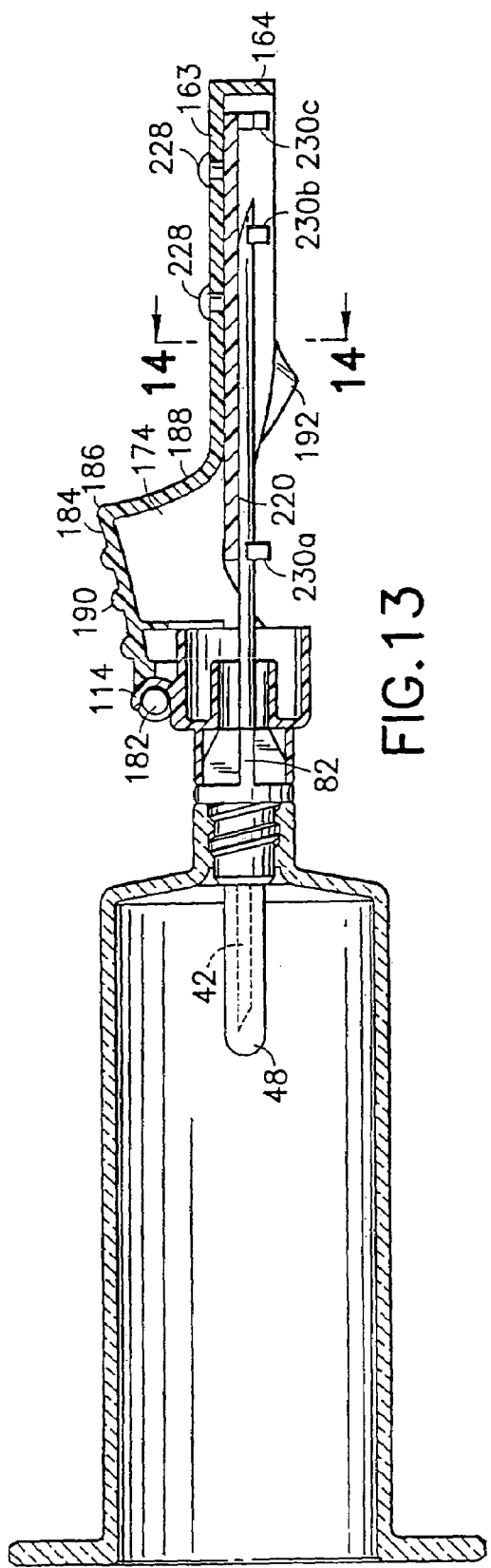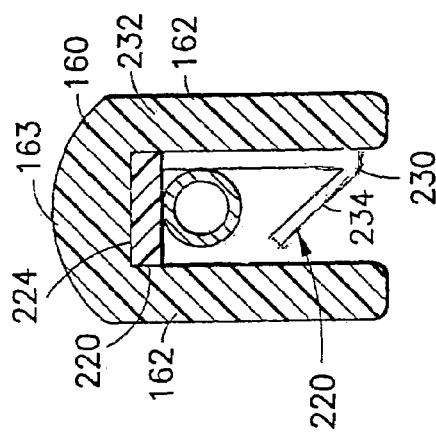

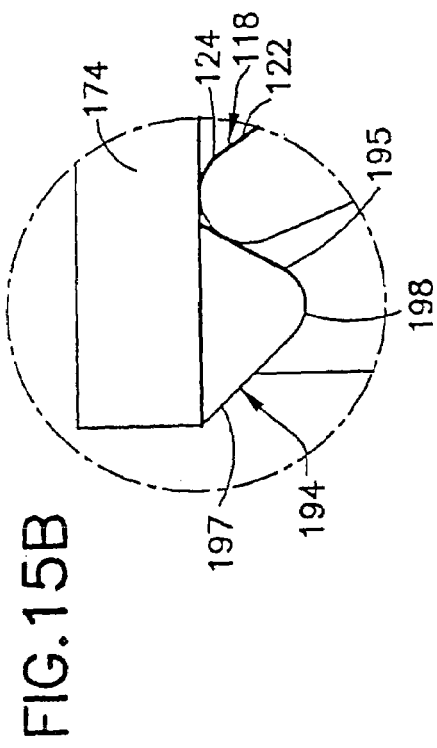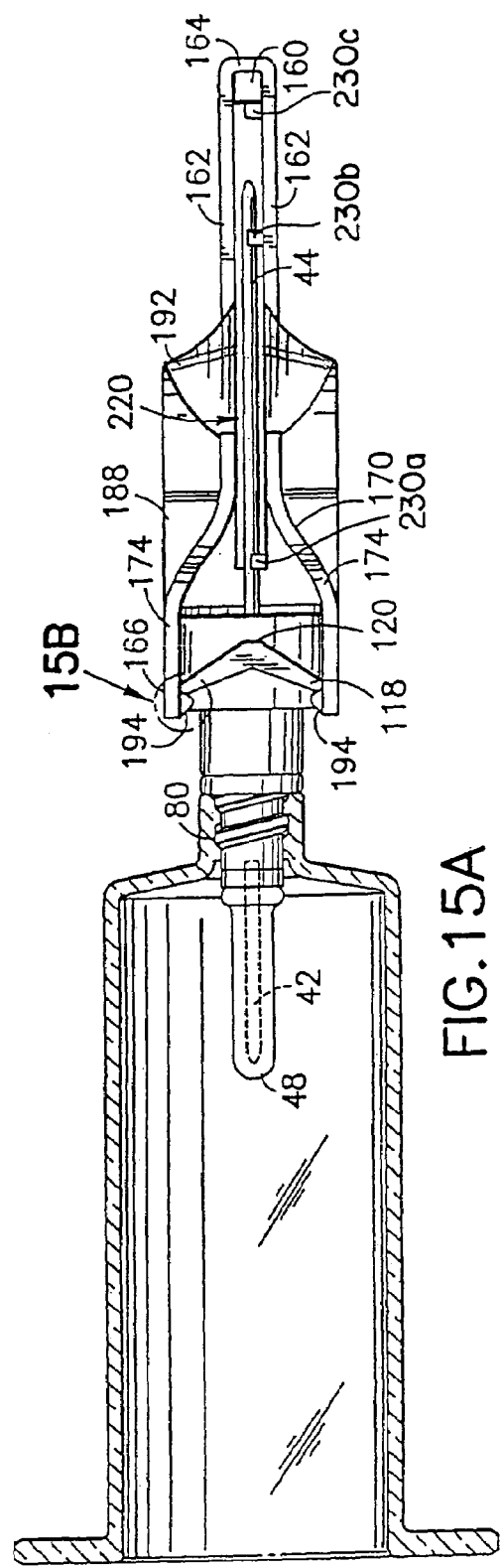
FIG.15B
FIG.15A

SAFETY NEEDLE ASSEMBLY

RELATED APPLICATION

This application is a continuation of U.S. patent application Ser. No. 10/170,318 which was filed Jun. 12, 2002 now U.S. Pat. No. 6,699,217.

FIELD OF THE INVENTION

The present invention relates to a shield for a needle and more particularly to a safety shield assembly that may be used in conjunction with a syringe assembly, a hypodermic needle, a needle assembly, a needle assembly with a needle holder, a blood collection needle, a blood collection set, an intravenous infusion set or other fluid handing devices or assemblies that contain piercing elements.

BACKGROUND OF THE INVENTION

Disposable medical devices having piercing elements for administering a medication or withdrawing a fluid, such as hypodermic needles, blood collecting needles, fluid handling needles and assemblies thereof, require safe and convenient handling. The piercing elements include, for example, pointed needle cannula or blunt ended cannula.

Safe and convenient handling of disposable medical devices is recognized by those in the medical arts so as to minimize exposure to blood borne pathogens. Safe and convenient handling of disposable medical devices results in the disposal of the medical devices intact.

As a result of this recognition, numerous devices have been developed for shielding needles after use. Many of these devices are somewhat complex and costly. In addition, many of these devices are cumbersome to use in performing procedures. Furthermore, some of the devices are so specific that they preclude use of the device in certain procedures or with certain devices and/or assemblies. For example, some devices employ very short thin needle cannulas. A shield designed to lock near the distal end of one needle cannula might not engage a much shorter needle cannula. Additionally, a shield designed to lock with a wider gauge needle cannula might be more likely to generate a spray upon engaging a much narrower needle cannula. Furthermore, it may be desirable to reduce the force required to effect shielding without reducing the audible and tactile indications of complete shielding.

Therefore, there exists a need for a safety shield assembly: (i) that is manufactured easily; (ii) that is applicable to many devices; (iii) that is simple to use with one hand; (iv) that can be disposed of safely; (v) that does not interfere with normal practices of needle use; (vi) that has tactile features whereby the user may be deterred from contacting the needle, the user may easily orient the needle with the patient and easily actuate and engage the shield assembly; (vii) that has visual features whereby the user may be deterred from contacting the needle, the user may easily orient the needle with the patient and easily actuate and engage the shield assembly; (viii) that is not bulky; (ix) that includes means for minimizing exposure to the user of residual fluid leaking from the needle; and (x) provides minimal exposure to the user because the needle shield is immediately initiated by the user after the needle is withdrawn from the patient's vein.

SUMMARY OF THE INVENTION

The present invention is a safety shield assembly that comprises: a shield; means for connecting the shield to a fluid handling device that contains a piercing element, such as needle; means for pivoting the shield away from the needle and means for securely covering and/or containing the needle within the shield.

Preferably, the shield comprises a rearward end, a forward end, a slot or longitudinal opening for housing the used needle in the forward end, means for securing the needle in the slot, means for guiding the needle into the slot, means for connecting the shield and the fluid handling device, means for guiding the user's fingers to move the shield into various positions, and means for retaining the shield securely over the used needle.

Desirably, the means for connecting the shield to the fluid handling device is a collar. Preferably, the shield is connected movably to a collar which is connected to a fluid handling device.

Preferably, the shield is connected to the collar by a hanger bar that engages with a hook arm on the collar so that the shield may be pivoted with respect to the collar into several positions. It is within the purview of the present invention to include any structure for connecting the shield to the collar so that the shield may be pivoted with respect to the collar. These structures include known mechanical hinges and various linkages, living hinges, or combinations of hinges and linkages.

Most preferably, the shield is connected to the collar by an interference fit between the hanger bar and the hook bar. Therefore, the shield always is oriented in a stable position and will not move forward or backwards unless movement of the shield relative to the hanger bar and the hook bar is initiated by the user.

Alternatively, the shield and collar may be a unitary one-piece structure. The one-piece structure may be obtained by many methods, including molding the shield and the collar as a one-piece unit, thereby eliminating the separate shield and collar during the manufacturing assembly process.

The assembly of the present invention may further comprise tactile and visual means for deterring the user from contacting the needle, providing easy orientation of the needle with the patient and providing the user with a guide for actuation and engagement with the shield.

The assembly of the present invention may further comprise means for minimizing exposure by the user to residual fluid leaking from a used needle. For example, a polymer material, such as a gel, may be located in the shield.

Most desirably, the assembly of the present invention is such that the cooperating parts of the assembly provide the means for the shield to move into a forward position over the needle. Thus, by simple movement of the shield into a forward position over the used needle, the assembly is ready for subsequent disposal. Therefore, the safety shield assembly of the present invention provides minimal exposure of the user to a needle because the shielding is initiated by the user immediately after the needle is withdrawn from the patient's vein.

Desirably, the assembly of the present invention may be used with a syringe assembly, a hypodermic needle, a needle assembly, a needle assembly with a needle holder, a blood collection set, an intravenous infusion set or other fluid handling devices. Preferably, the assembly of the present invention is used with a needle assembly comprising a needle and a hub. Preferably the needle is a conventional double ended needle.

Most preferably, the present invention is used with a needle assembly comprising a hub and a needle connected to the hub whereby the needle comprises a non-patient end and an intravenous end. The collar of the present invention may comprise a hook arm and the shield may be connected movably to the hook arm. Thus the shield may be pivoted with respect to the collar and moved easily into several positions.

Preferably, the collar is fitted non-rotatably with the hub of the needle assembly. Additionally, the collar includes cooperating means that mate with reciprocal means on the shield to provide a clear audible and tactile indication of complete shielding. The cooperating means on the collar may include generally chevron-shaped projection formed on a side of the collar substantially diametrically opposite the hook arm or other such structure that provides the hinge connection to the shield. The chevron-shaped structure includes a forward or distal point. Slanting surfaces diverge and extend proximally from the distal point. The slanting surfaces cooperate with the reciprocal means on the shield to generate a deflection of the sidewalls of the shield away from one another. The chevron-shaped structure further includes proximal ends that are convexly arcuate. The convexly arcuate ends of the chevron-shaped structure on the collar cooperate with the reciprocal means on the shield and with the resiliently deflectable sidewalls of the shield to generate the tactile and audible indication of shielding.

The means for securely locking the shield in the second position comprises a clip secured to the interior of the shield. The clip preferably includes an elongate base with means for attachment to the shield and a plurality cannula finger locks extending from the base for locked engagement with the cannula when the shield is in the second position around the needle cannula. Each cannula finger lock preferably includes a support leg that projects from the base and a cannula engaging leg or detent that extends from the free end of the support leg. Each cannula finger lock is dimensioned, disposed and aligned to contact the needle cannula when the shield approaches the second position. Contact between the cannula and each cannula finger lock may cause each cannula finger lock and/or the needle cannula to deflect resiliently. Sufficient rotation of the shield will cause the needle cannula to pass the cannula engaging legs. As a result, each cannula finger lock and/or the needle cannula will resiliently return to or toward its undeflected condition for securely trapping the needle cannula in the shield. The means for attaching the clip to the shield may comprise apertures in the shield and snaps or other locking projections formed on the base of the clip. The snaps can be force fit through the apertures in the shield. Alternatively, the means for the clip to the shield may comprise apertures in the clip and snaps or other locking projections formed on the shield. The number and location of the cannula finger locks may be selected in view of the length of the needle. At least two and preferably three cannula finger locks may be provided.

Preferably, the collar is fitted with the hub of the needle assembly so that the collar cannot rotate around the hub. Alternatively, the collar and hub may be a unitary one-piece structure. The one piece structure may be accomplished by many methods including molding the collar and the hub as a one-piece unit thereby eliminating the need to separately assemble the collar to the hub during the manufacturing process.

Most preferably, the collar is fitted with the hub of the needle assembly so that the bevel surface or bevel up surface of the intravenous or distal end of the needle faces the same side of the collar when the shield is in the first position. Alignment of the collar, hub, shield and needle with the bevel surface up makes it easier to insert the needle into the patient without manipulating the assembly. The orientation of the intravenous end of the needle with the bevel up assures the user that the needle is properly oriented for use and does not require any manipulation before use. Most notably, the orientation of the shield provides a visual indication to the user of the orientation of the bevel surface of the needle.

Preferably, the shield is capable of pivoting from a first position where the intravenous end of the needle is exposed and bevel up, to an intermediate position where the needle is partially covered, to a second position where the needle is covered completely.

Alternatively, it is within the purview of the present invention that the shield, collar and hub is a unitary one-piece structure. The one-piece structure may be accomplished by many methods including molding the shield, collar and hub as a one-piece unit thereby eliminating the need to separately assemble the shield, collar and hub during the manufacturing process.

It is an advantage of the present invention that the shield covering the used intravenous end of the needle provides easy containment of the used needle. A further advantage of the shield is that it will only move upon initiation by the user.

The assembly of the present invention when used with a fluid handling device is also easily disposable when removed from a conventional needle holder, or other such device.

A notable attribute of the present invention is that it is easily adaptable with many devices. For example, the invention is usable with syringe assemblies, hypodermic needles, needle holders, blood collection needles, blood collection sets, intravenous infusion sets such as catheters or other fluid handling devices or assemblies that contain piercing elements.

Another notable attribute of the present invention is that the tactile and visual features deter the user from touching the needle, allow the user to easily orient the needle with the patient and guide the user to actuate and engage the shield of the assembly.

BRIEF DESCRIPTION OF THE DRAWINGS

FIG. 1 is a perspective view of the safety shield assembly of the present invention as connected to a needle assembly and related packaging features.

FIG. 2 is a perspective view of the unassembled pieces of FIG. 1.

FIG. 3 is a bottom view of the shield as shown in FIG. 2.

FIG. 4 is a cross sectional view of the collar as shown in of FIG. 2 taken along lines 4—4 thereof.

FIG. 13 is a cross sectional view of the assemblies in use with a conventional needle holder as shown in FIG. 12 taken along lines 13—13 thereof.

FIG. 14 is a cross-sectional view of the assemblies of FIG. 13 taken along lines 14—14 thereof.

FIG. 15 is a bottom view of the assemblies as shown in FIG. 11.

DETAILED DESCRIPTION OF THE INVENTION

Figure 5:
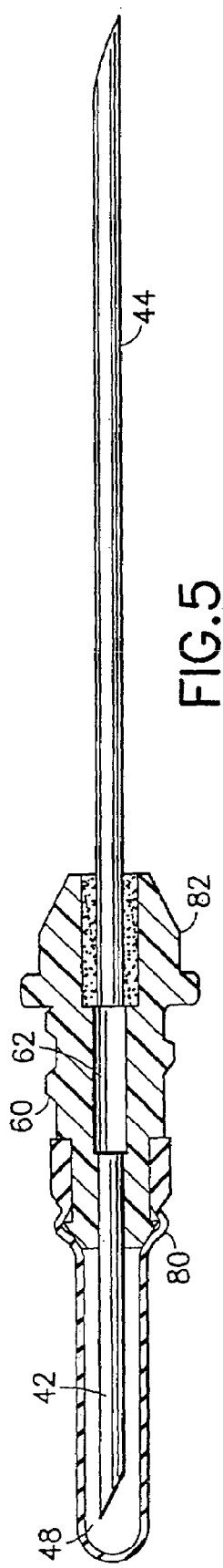
FIG. 5 is a cross sectional view of the needle hub as shown in FIG. 2 taken along lines 5—5 thereof.

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

Referring to the drawings in which like reference characters refer to like parts throughout the several views thereof, FIGS. 1 and 2 illustrate a needle assembly with the safety shield assembly of the present invention and the related packaging features. The needle assembly includes a needle 40, a hub 60, packaging features to cover the needle and a label. The safety shield assembly includes a collar 90 and a shield 140.

As shown in FIGS. 2 and 5, needle 40 includes a non-patient end 42, an intravenous end 44 and a passageway 46 extending between the non-patient end and the intravenous end. An elastomeric sleeve 48 covers the non-patient end. A first rigid sleeve 50 covers the intravenous end and a second rigid sleeve 52 covers the non-patient end and the elastomeric sleeve. As shown in FIG. 1, a label 196 may also be applied to the finally assembled parts.

As shown in FIGS. 2 and 5, hub 60 includes a threaded end 64, a ribbed end 66 and passageway 62 extending between the threaded end and the ribbed end. Threaded end 64 and ribbed end 66 are separated by flange 68. Non-patient end 42 of needle 40 extends from threaded end 64 and intravenous end 44 of needle 40 extends from ribbed end 66. Preferably, threaded end 64 comprises male threads 80 for mounting the hub on a conventional needle holder and ribbed end 66 comprises male ribs 82 for connecting the hub and collar 90.

As shown in FIGS. 2 and 4, collar 90 includes a forward skirt 92 and a rearward skirt 94. Forward skirt 92 is cylindrical and comprises an inner circumferential surface 96 and an outer circumferential surface 98. Forward skirt 92 mates with rearward skirt 94 at a shoulder 100. Rearward skirt 94 is cylindrical and comprises an inner circumferential surface 102 and an outer circumferential surface 104 and extends from shoulder 100 opposite of forward skirt 92. The inner diameter of forward skirt 92 is larger than the inner diameter of rearward skirt 94. Alternatively, the inner diameters for collar 90 can be equal. A hook 114 extends from outer circumferential surface 98 of forward skirt 92. Additionally a chevron-shaped protrusion 118 projects outwardly from outer circumferential surface 98 of forward skirt 92 at a side opposite hook 114. The chevron-shape protrusion 118 is substantially symmetrical and has a peak 120 pointed toward forward skirt 92 and ramp surfaces 122 that diverge symmetrically from peak 120 toward rearward skirt 94. Ramp surfaces 122 terminate at rounded ends 124 at the outer side and proximal extremes of chevron-shaped protrusion 118. Rounded ends 124 extend continuously into the proximal side of chevron-shaped protrusion 118 facing toward rearward skirt 94.

Figure 6:
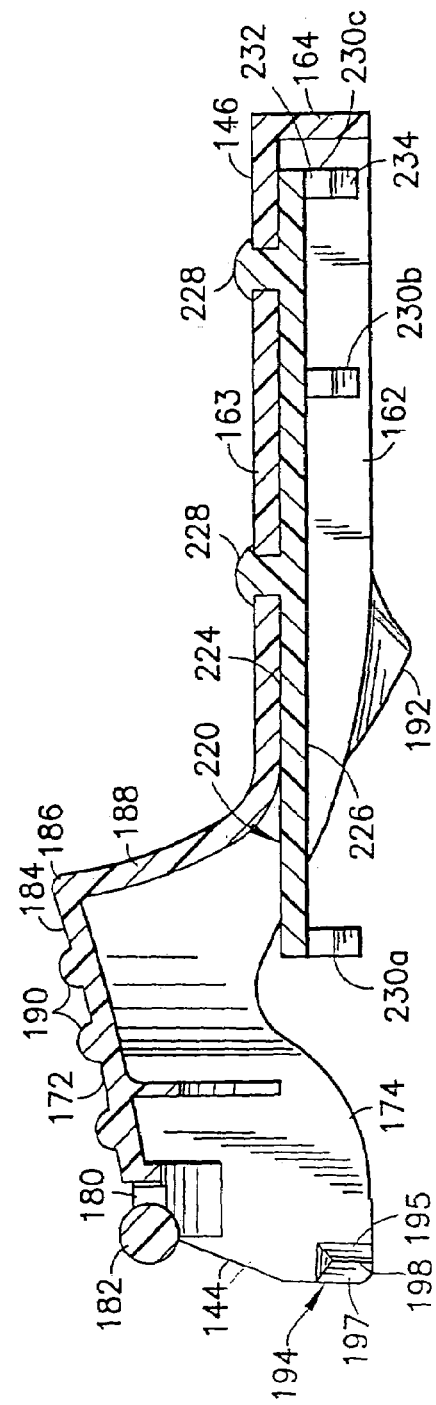
FIG. 6 is a cross sectional view of the shield of FIG. 2 taken along lines 6—6 thereof.
Figure 7:
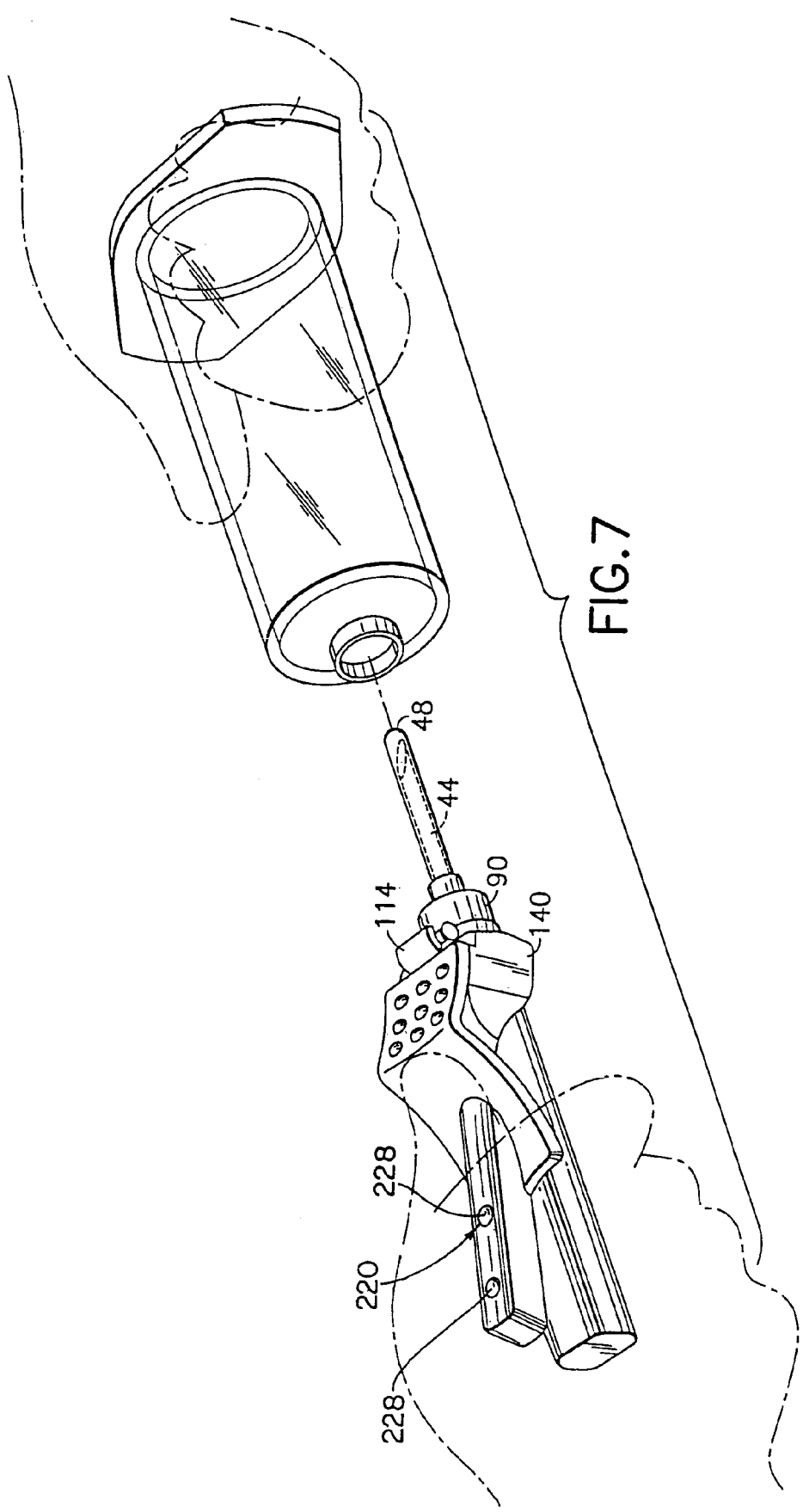
FIGS. 7–12 illustrate the use of the safety shield assembly with the needle assembly of FIG. 1 with a conventional needle holder.
Figure 8:
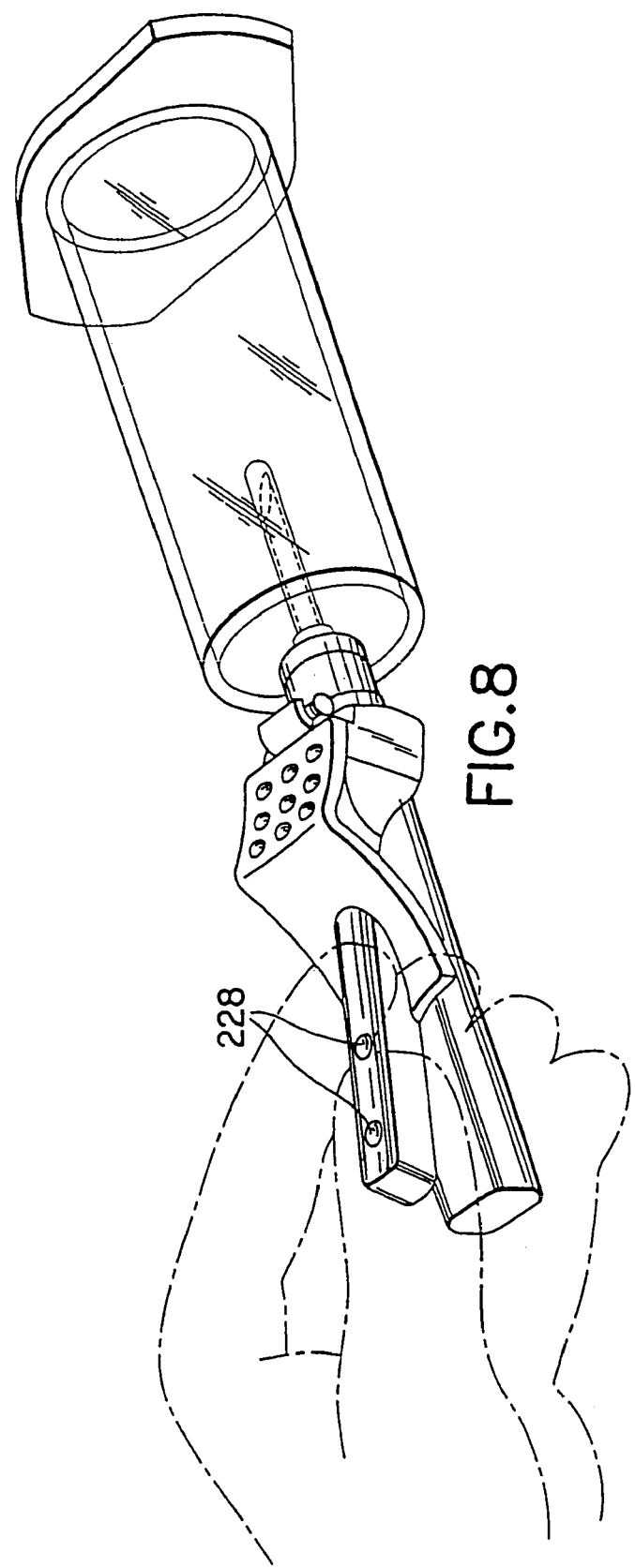

As shown in FIGS. 2 and 6, shield 140 comprises a rearward end 144 and a forward end 146. Forward end 146 of shield 140 includes a slot or longitudinal opening 160 formed by sidewalls 162 that extend downwardly from top wall 163 and run substantially opposite of one another in parallel along the length of slot 160 towards forward end wall 164. Slot 160 is slightly wider than needle 40. Sidewalls 162 include bottom edges 165 that extend substantially parallel to one another and parallel to top wall 163. Top wall 163 is formed to include two longitudinally spaced apertures 167 extending entirely therethrough.

Shield 140 further includes a clip 220. Clip 220 includes an elongate base 222 having a width less than the distance between sidewalls 162 at forward end 146 of shield 140. Base 222 includes opposite top and bottom surfaces 224 and 226. Top surface 224 is configured to nest closely with the inner surface of top wall 163 of shield 140. Top surface 224 is characterized by mounting projections 228. Mounting projections 228 are disposed and configured to be snap fit through apertures 167 in top wall 163 of shield 140. More particularly, each mounting projection 228 includes a head that is tapered to a cross-sectional dimension slightly greater than the inside cross-sectional dimension of the respective aperture 167 in top wall 163. Thus, the head of mounting projection 228 and portions of top wall 163 adjacent apertures 167 will yield slightly as mounting projections 228 are forced through apertures 167. Top wall 163 and mounting projections 228 will return resiliently to their initial position after the enlarged heads passed through apertures 167. Hence, base 222 of clip 220 will be held securely adjacent top wall 163 of shield 140.

Clip 220 is characterized further by a plurality of cannula finger locks 230a, 230b and 230c projecting from bottom surface 226 of base 222. Each cannula finger lock 230 includes a support leg 232 and a locking finger 234. Cannula finger locks 230 can take any of several optional constructions. For example, support leg 232 can be substantially rigid with respect to base 222 and locking finger 234 can be substantially rigid with respect to support leg 232. In these situations, cannula finger locks 230 will function to deflect needle 40 resiliently and then to trap needle 40 beneath locking finger 234. Alternatively, the support leg 232 can be resiliently deflectable relative to base 222. Thus, the support leg 232 may deflect relative to base in response to forces generated by contact with needle 40. Support leg 232 then will return resiliently to an undeflected condition so that locking finger 234 engages and traps needle 40. This embodiment requires base 220 to be sufficiently narrow to permit deflection of support leg 232. As a further option, locking finger 234 may be configured to deflect resiliently relative to support leg 232. Still further, both support leg 232 and locking finger 234 may be resiliently deflectable.

Base 222, as shown most clearly in FIGS. 3 and 6 is longer than top wall 163 of forward end 146 of shield 140. Hence, base 222 includes a distal end 236 near forward end wall 164 and a proximal end 238 that extends into rearward end 144 of shield 140. Cannula finger lock 230a is disposed near proximal end 238 of base 222 and in rearward end 144 of shield 140. As a result, proximal cannula finger lock 230a is particularly useful for needle assemblies that employ a very short needle 40. Of course, however, cannula finger locks 230b and 230c also can be employed in situations where needle 40 is longer.

Broken line 240 in FIG. 2 shows an optional proximal end for base 222. Base 222 with a proximal end at line 240 can be used with needle assemblies known to employ the long needle 40. In this embodiment, base 222 does not extend into rearward end 144 of shield 140.

Rearward end 144 of shield 140 defines a collar engaging area 166 that is a continuation of slot 160. Collar engaging area 166 includes a rearward end 168, a forward end 170, a top finger guide area 172, sidewalls 174 that extend downwardly from top finger guide area 172, an underside area 176 dimensioned for surrounding collar 90, and extending arms 180 to support hold hanger bar 182. Sidewalls 174 are spaced apart by a major width adjacent rearward end 168. The major width is selected to enable sidewalls 174 to slide across diametrically opposite side surfaces of forward skirt 92 of collar 90. Sidewalls 174 converge, however, toward forward end 170 to define a minor distance therebetween substantially equal to the distance between sidewalls 162 at forward end 146 of shield 140. Sidewalls 174 include bottom edges 177 that face away from top finger guide area 172. As shown most clearly in FIG. 6, bottom edges 177 curve toward top finger guide area 172 at locations between rearward end 168 and forward end 170 of collar engaging area 166.

The extreme rear ends of sidewalls 174 on collar engaging area 166 include rounded ears 194 that project toward one another from opposed inner surfaces 175 of sidewalls 174. Rounded ears 194 are disposed to engage chevron-shaped projection 118 on collar 90. More particularly, each rounded ear 194 includes a distal surface 195, a proximal surface 197 and a curved surface 198 extending between distal and proximal surfaces 195 and 197. Distal surface 194 is aligned to sidewall 174 at a rake angle of approximately 60° and proximal surface 197 is aligned to sidewall 174 at an angle of approximately 45°. Curved surface 198 extends smoothly and convexly between distal and proximal surfaces 195 and 197. Proximal surfaces 197 of rounded ears 194 will engage ramp surfaces 122 of chevron-shaped projection 118 to deflect sidewalls 174 slightly away from one another as shield 140 approaches the second position. The apex of curved surface 198 on each rounded ear 194 passes the respective rounded end surface 124 on chevron-shaped projection 118 on collar 90. As a result, sidewalls 174 begin to return resiliently toward an undeflected condition. The resilient return of sidewalls 174 and raked distal surface 195 of ears 194 also causes sidewalls 174 to snap against chevron-shaped projection 118. This snapping action provides a clear audible and tactile indication of complete shielding and occurs substantially when the used needle is trapped by cannula finger locks 230. The angles of distal and proximal surfaces 195 and 197 of rounded ears 194 affects the performance of shield 140. In particular, a smaller acute angle alignment of proximal face 197 reduces the force required to move shield 140 passed rounded ears 194. A larger acute angle proximal surface 197 of rounded ears 194 requires a greater force to move shield 140 toward the second position. Similarly, the angle between distal surface 195 and sidewall 174 affects the acceleration characteristics as shield 140 is propelled toward the second position in response to the resilient return of sidewalls 174 and hence affects the audible indication of shielding.

Top finger guide area 172 comprises a first ramp 184 that extends slightly on an upwardly slope from the rearward end of the collar engaging area to a shoulder 186. From shoulder 186 extends a second ramp 188 which slopes downwardly towards top section 163. Most preferably, first ramp 184 comprises touch bumps 190. The touch bumps provide a tactile and visual guide to alert the user that the user's finger has contacted the shield and that the shield is in a defined or controlled position. The touch bumps may be any configuration so long as they extend and are distinct from the top finger guide area. The touch bumps may also be of a distinguishing color as compared to the top finger guide area or the shield.

Second ramp 188 has interior surface 192 for urging the needle toward the center of slot 160 as the shield is being rotated into the second position. The exterior surfaces are slightly inclined and extending radially from the second ramp. The interior surfaces are especially helpful if the longitudinal axis of the needle is misaligned with respect to the longitudinal axis of the hub.

Extending arms 180 are located at rearward end 168 and at the beginning of top finger area 172 and hold hanger bar 182.

The safety shield assembly and the needle assembly are assembled together whereby needle 40 is connected to hub 60 and sealed with adhesive at the ends of the hub. Hub 60 is then joined with collar 90 by ultra-sonic welding techniques or any other bonding techniques, or mechanical fit, whereby rearward annular skirt 94 of collar 90 mates with ribbed end 66 of the hub. Male ribs 82 of the hub are contained or forced fitted within inner sidewall 102 of rearward annular skirt 94 of collar 90. The collar is aligned with the intravenous end of the needle whereby the hook arm is aligned with the bevel up of the needle. Then rigid sleeve 50 is force fitted into inner side wall 96 of forward skirt 92 of collar 90 to cover the needle. Clip 220 is mounted into shield 140 by forcing mounting projections 228 through mounting apertures 167 in shield 140. Thereafter, shield 140 is connected to collar 90 whereby hanger bar 182 is force fitted into hook member 114 whereby slot 160 faces rigid sleeve 50. Most preferably, the shield is connected to the collar by a force fit or interference fit between the hanger bar and the hook bar. Therefore, the shield is always oriented in a stable position and will not move unless movement of the shield is positively initiated by the user. To assemble the last piece, shield 140 is moved towards rigid sleeve 50 and second rigid sleeve 52 is force fitted onto outer sidewall 104 of rearward skirt 94 of collar 90.

In addition, a label 196 may be applied to the finally assembled parts. The label may be used to provide tamper resistance of the parts, so that they are not reused.

Figure 9:
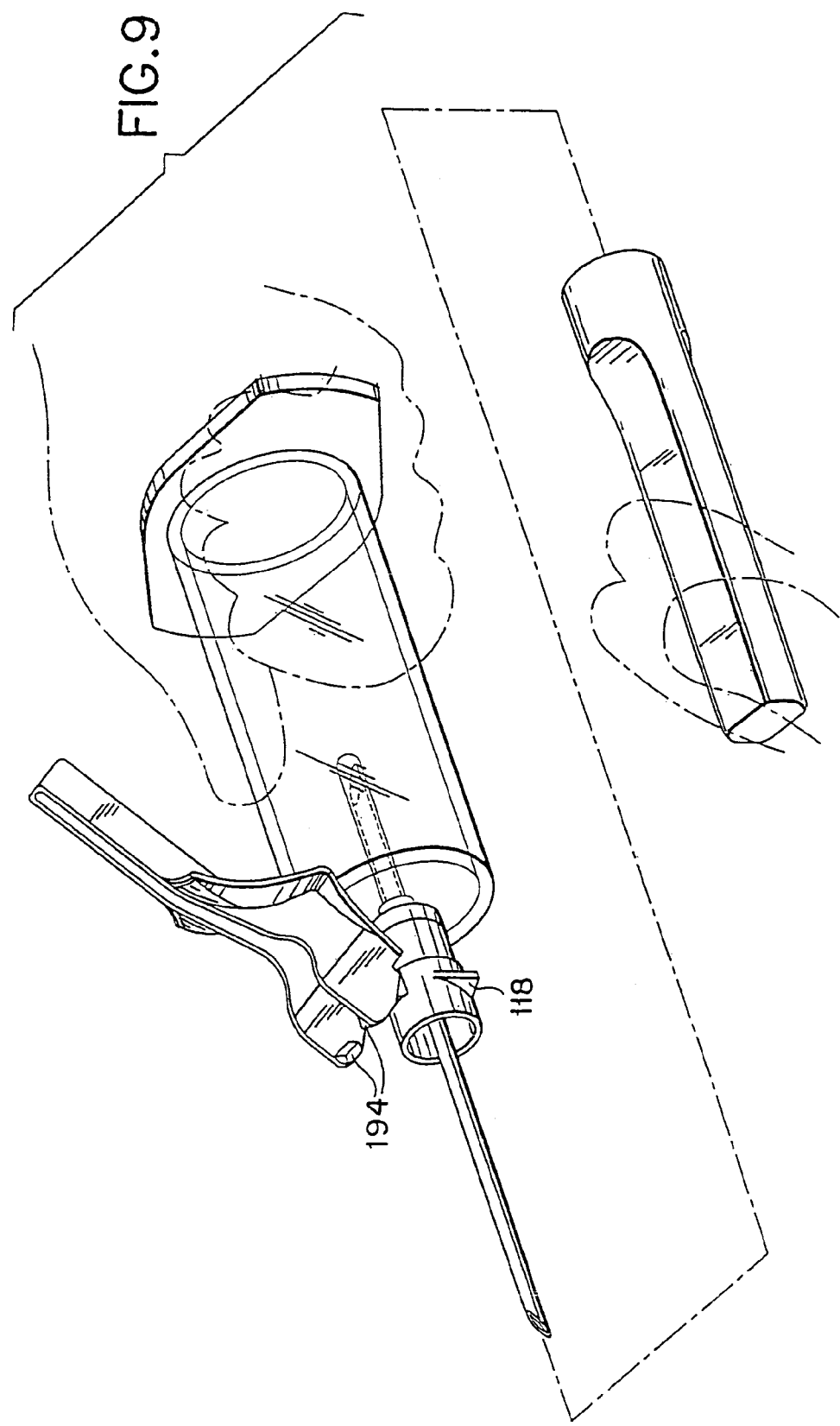
Figure 10:
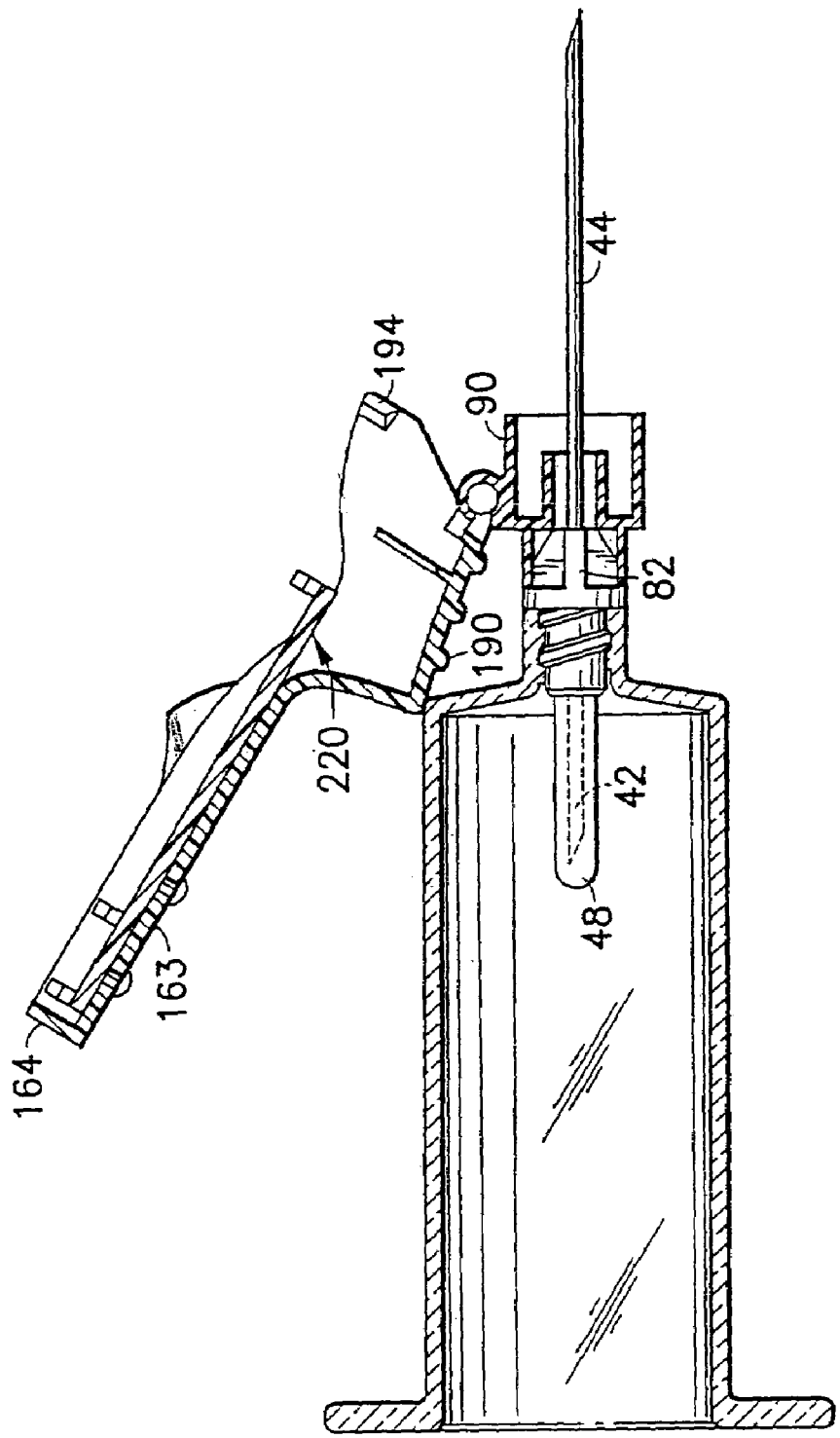
Figure 11:
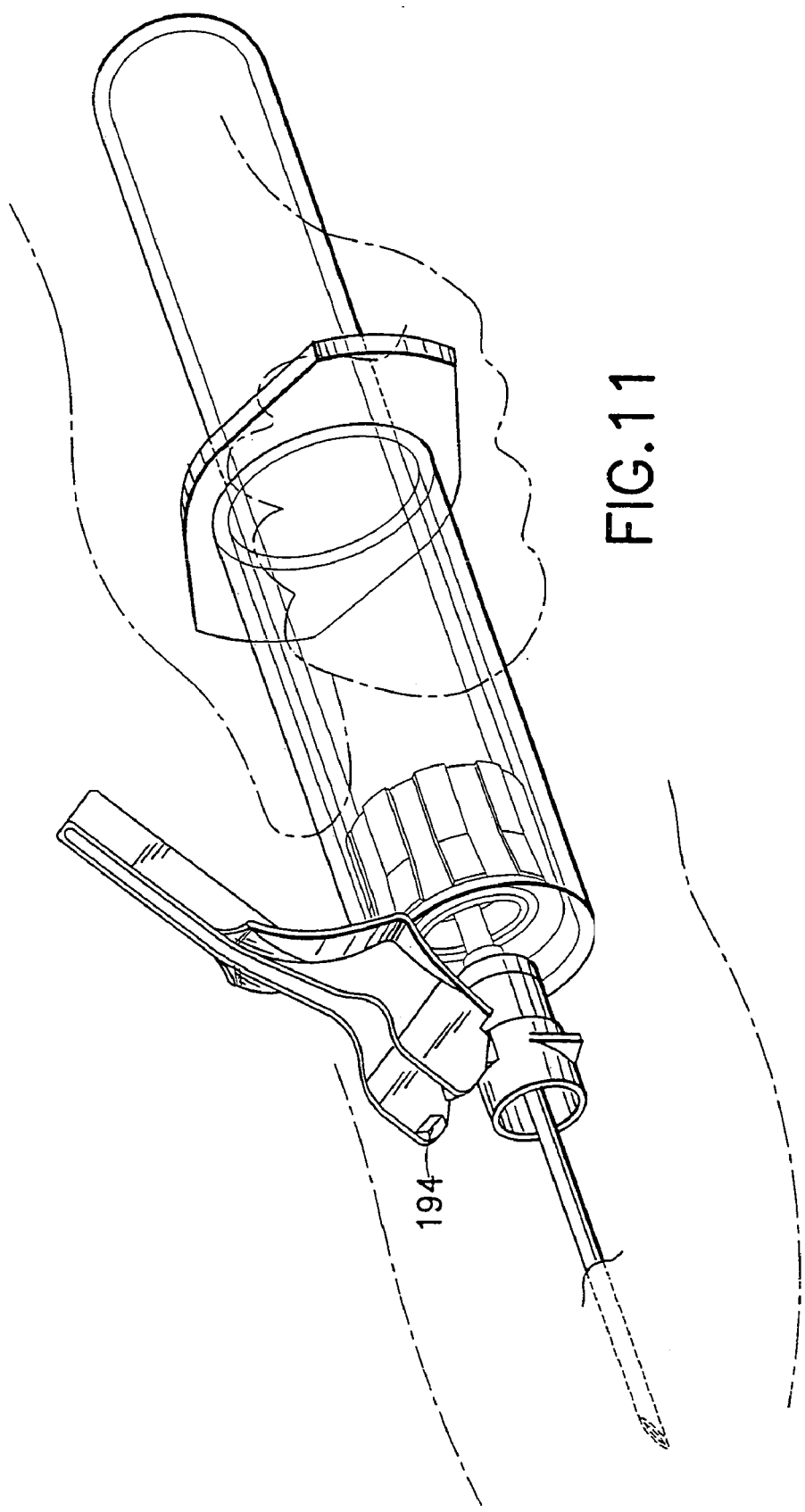
Figure 12:
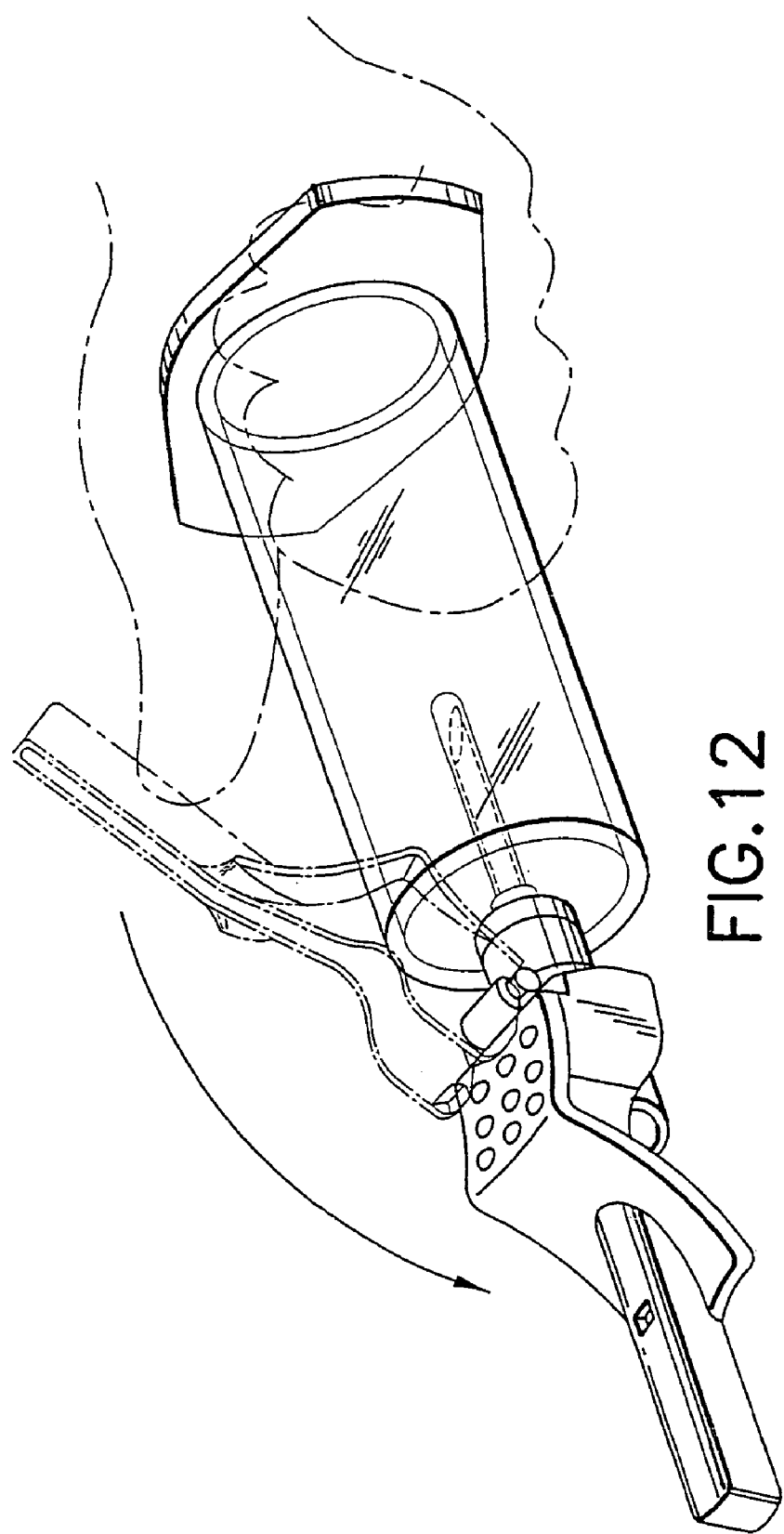

In use, as shown in FIGS. 7–15, the non-patient needle shield is removed and then a needle holder is screwed onto the hub of the needle. As specifically shown in FIGS. 8 and 12 the shield is then rotated back by the user towards the needle holder. Then as shown in FIG. 9, the intravenous needle shield is removed from covering the intravenous needle. Then as shown in FIG. 10, a venipuncture is conducted whereby the intravenous end of the needle is inserted into a vein of a patient and an evacuated tube having a closure is inserted into the needle holder. Then as shown in FIGS. 11 and 13, when the venipuncture is complete the user easily rotates the shield from the first position towards the intravenous needle to an intermediate position and then the user pushes on the shield at the top finger guide area to move the shield into a second position whereby the needle is trapped in the longitudinal opening. More particularly, needle 40 contacts cannula finger locks 230a–c of clip 220. The engagement of needle 40 with cannula finger locks 230a–c causes cannula finger locks 230a–c to deflect sufficiently to pass needle 40. As a result, cannula finger locks 230a–c will return resiliently to an undeflected condition. Thus, needle 40 will be trapped between cannula finger locks 230a–c and base 222. The deflection of cannula finger locks 230a–c can occur in the support legs 232 and/or the locking fingers 234. Alternatively, cannula finger locks 230a–c can be substantially rigid structures that generate deflection of needle 40 sufficient for needle 40 to pass locking fingers 234. Needle 40 then will return resilient to an undeflected condition and will be trapped between locking fingers 234 and base 222.

Needle 40 is contained within shield 140 as the shield is pivoted into the second position. More particularly, proximal surfaces 197 of rounded ears 194 move over ramp surfaces 122 of chevron-shaped projection 118 and cause sidewalls 174 to deflect away from one another. The angularly aligned proximal faces 197 of rounded ears 194 ensure easy movement of shield 140. Additionally, the resiliency of sidewalls 174 and the angular alignment of distal surface 195 of ears 194 causes a cooperation with rounded proximal ends 124 of chevron-shaped projection 118 to accelerate shield 140. This accelerated movement of shield 140 helps to generate a clear audible and tactile indication of complete shielding.

Figure 16:
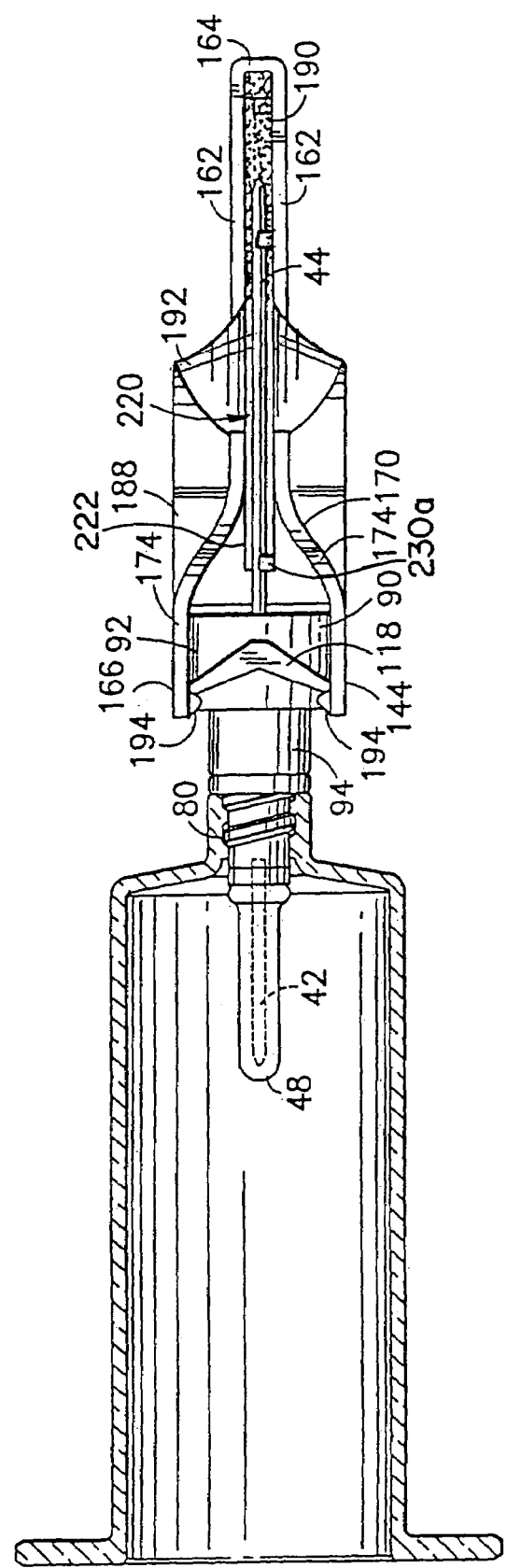
FIG. 16 illustrates an additional embodiment of the present invention, whereby a gel material is located in the shield as shown in a bottom view of the assemblies of FIG. 11.

Alternatively as shown in FIG. 16, a gel material 190 is located in shield 140 so that when the needle snaps past cannula finger locks 230 it will come to rest in gel material 190. The gel material will contain any residual fluid that may be on the needle. Simultaneously, rounded ears or projections 198 move over rounded proximal ends 124 of chevron-shaped projection 118. This causes sidewalls 174 to deflect away from one another and then to snap back into engagement with collar 90 to provide a clear audible and tactile indication of complete shielding.

Figure 17:
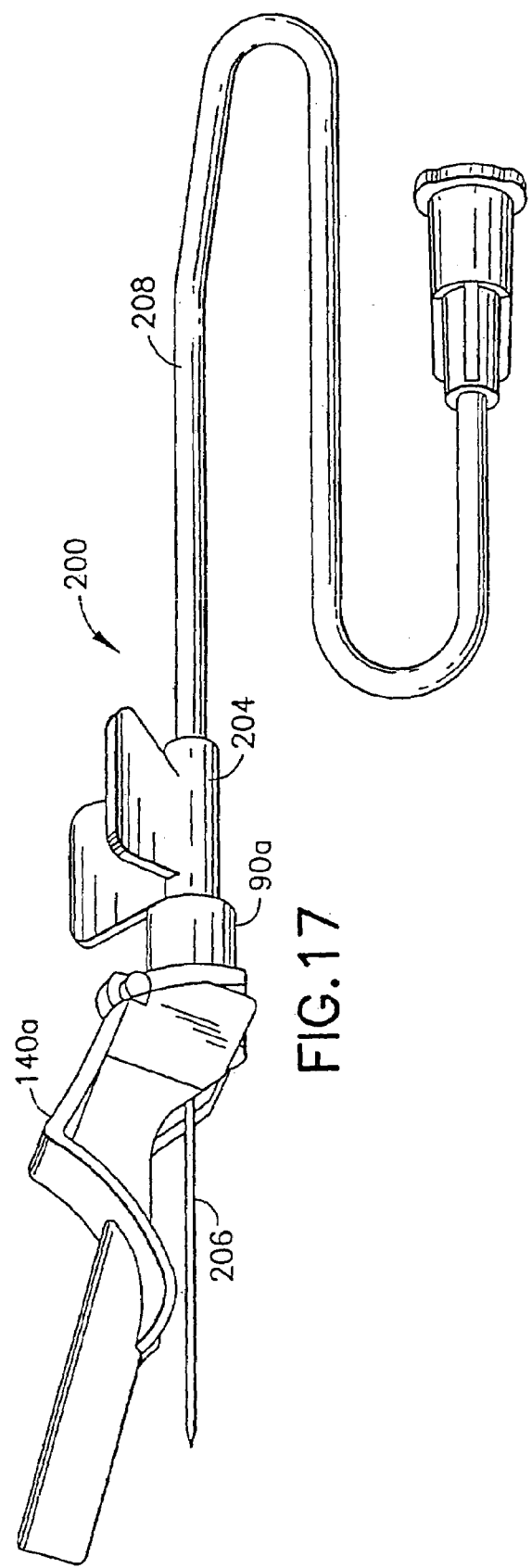
FIG. 17 is a perspective view of an additional embodiment of the present invention in use with a blood collection set.
Figure 18:
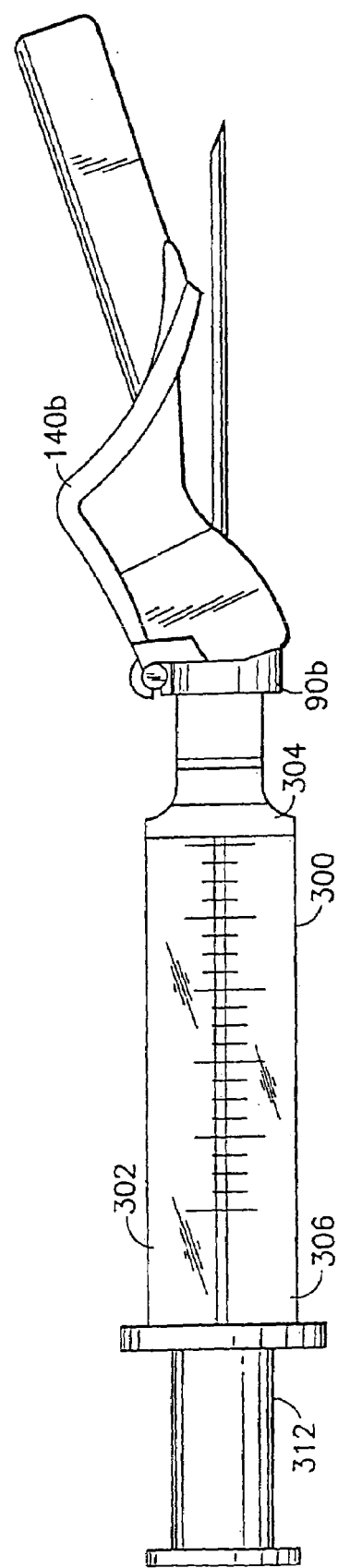
FIG. 18 is a perspective view of an additional embodiment of the present invention in use with a syringe.
Figure 19:
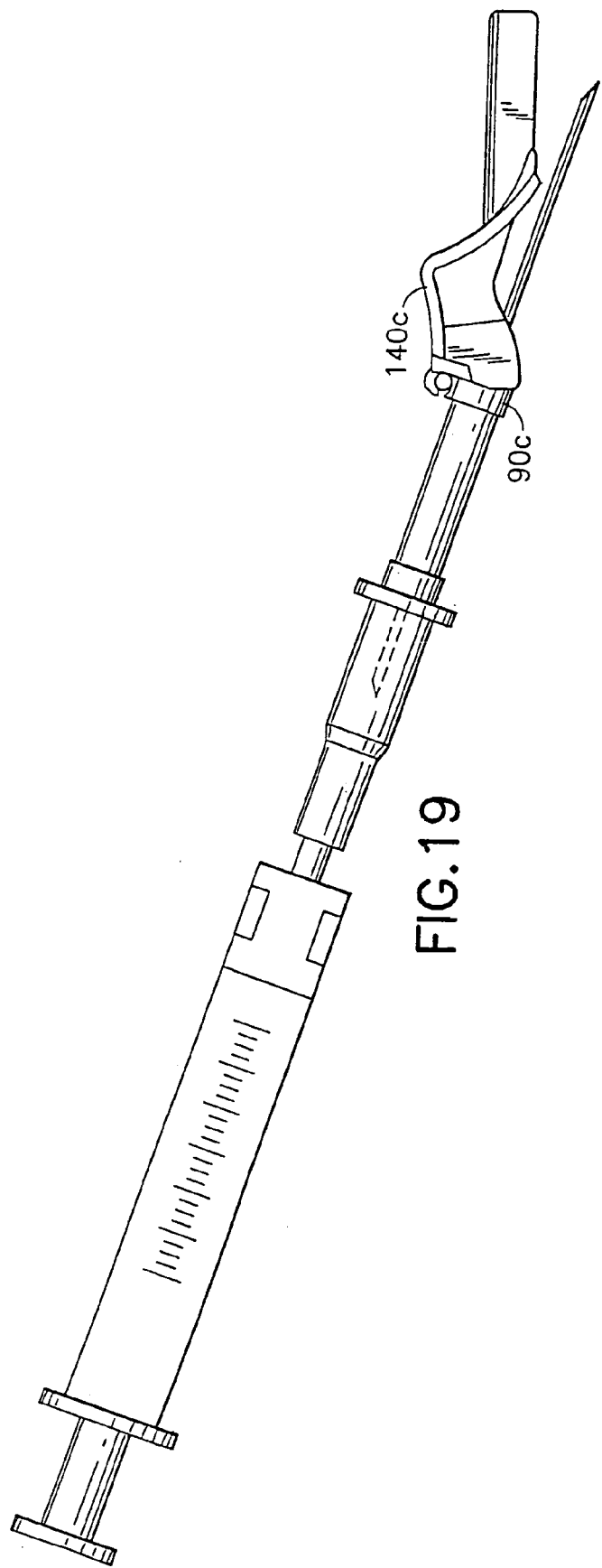
FIG. 19 is a perspective view of an additional embodiment of the present invention in use with a catheter.

FIGS. 17, 18, and 19 are further embodiments of the invention that may include components which are substantially identical to the components of FIGS. 1–3. Accordingly, similar components performing similar functions will be numbered identically to those components of FIGS. 1–3, except that a suffix "a" will be used to identify those similar components in FIG. 17, a suffix "b" will be used to identify those similar components in FIG. 18 and a suffix "c" will be used to identify those similar components in FIG. 19.

Alternatively, the safety shield assembly of the present invention may be used in conjunction with a conventional intravenous (IV) infusion set, as illustrated in FIG. 17.

For purposes of illustration, shield 140a and collar 90a are connected to a conventional IV infusion set, 200, or butterfly structure comprising a needle body with a needle hub 204 extending from the forward end of the needle body and a needle 206 embedded in hub 204. Extending from the rearward end of the needle body is flexible tubing 208 which is conventional and utilized to allow the user to manipulate the structure and to connect it subsequently to supplies of infusion liquids or for the return of collected blood if the arrangement is being used to collect blood.

Infusion set 200 further comprises flexible wings 210 attached to and projecting outwardly from needle hub 204.

Alternatively, the safety shield assembly of the present invention may be used in conjunction with a syringe, as illustrated in FIG. 18.

For purposes of illustration, shield 140b and collar 90b are connected to a conventional hypodermic syringe 300 comprising a syringe barrel 302 having a distal end 304 a proximal end 306 and a plunger 312.

Alternatively, the present invention may be used in conjunction with a catheter as illustrated in FIG. 19.

Figure 20:
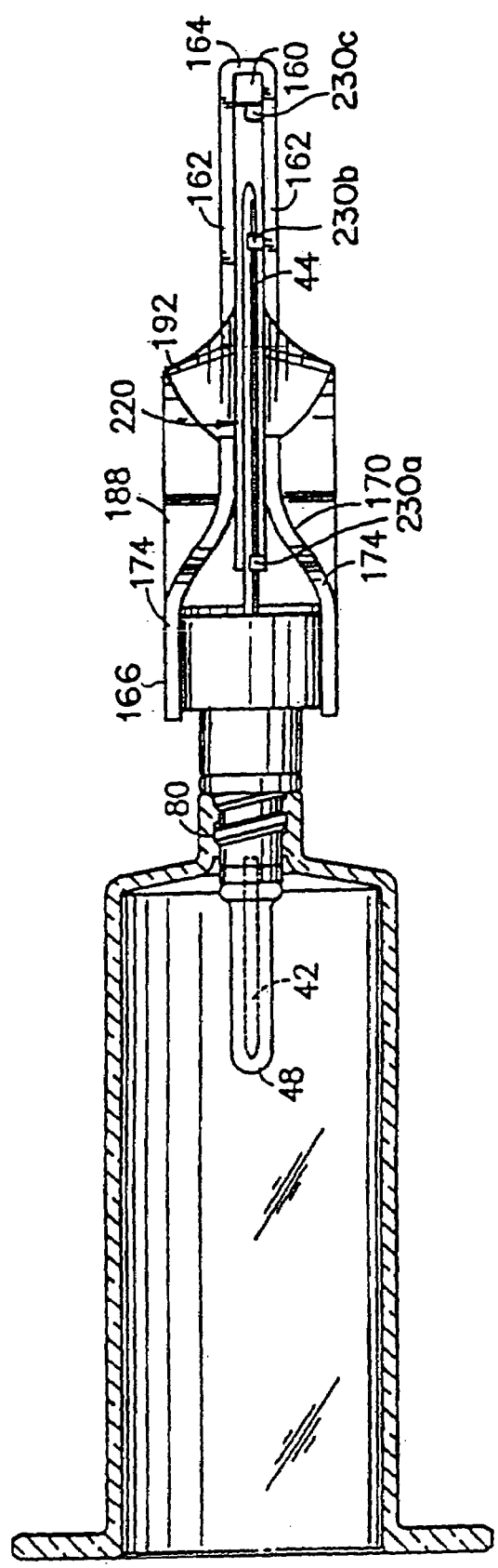
FIG. 20 is a bottom view similar to FIG. 15, but showing an additional embodiment of the present invention.

A further alternate embodiment is illustrated in FIG. 20, and is virtually identical to the embodiment of the invention depicted in FIG. 15A. As a result, comparable numerals have been employed to identify identical or very similar components. FIG. 20, however, differs from FIG. 15A in that collar 90 does not have the chevron-shaped protrusion 118 illustrated in FIG. 15A. Additionally, shield 140 does not have ears comparable to rounded ears 194 of FIG. 15A. Thus, the embodiment illustrated in FIG. 20 relies entirely upon the engagement of cannula finger locks 220 with needle 40. There are fewer structures on the embodiment of FIG. 20 to achieve the audible and tactile indication of complete shielding, as in the previous embodiment, and no structure for accelerating shield 140 into the second position around needle 40. However, upon complete shielding, the retention between shield 140 and needle 40 in the embodiment of FIG. 20 is comparable to the attention achieved by the previous embodiments.

The shield and collar of the safety shield assembly of the present invention are comprised of moldable parts which can be mass produced from a variety of materials including, for example, polyethylene, polyvinyl chloride, polystyrene or polyethylene and the like. Materials will be selected which will provide the proper covering and support for the structure of the invention in its use, but which will provide also a degree of resiliency for the purpose of providing the cooperative movement relative to the shield and the collar of the assembly.

What is claimed is:

1. A safety needle assembly comprising a needle hub with proximal and distal ends and a passage extending between said ends, a needle cannula mounted to said passage of said needle hub and having a pointed distal end projecting beyond said distal end of said hub, a shield having proximal and distal ends, said proximal end of said shield being hingedly mounted to said hub for rotation from a first position where said shield is spaced from said needle cannula to a second position where said shield substantially shields said needle cannula, said shield comprising a top wall, and opposed first and second sidewalls extending from said top wall, said shield including a rearward portion adjacent said proximal end of said shield configured for partly enclosing said hub and a forward portion adjacent said distal end of said shield configured for partly surrounding said needle, said rearward portion being cross-sectionally larger than said forward portion, a clip having an elongate base mounted to said top wall of said shield, a plurality of cannula finger locks projecting from said base of said clip and configured for locked engagement with said needle when said shield is rotated to said second position.

2. The safety needle assembly of claim 1, wherein said clip lies entirely within said forward portion of said shield.

3. The safety needle assembly of claim 1, wherein said base of said clip includes a proximal end disposed in said rearward portion of said shield, at least one of said cannula finger locks projecting from said proximal end of said base.

4. The safety needle assembly of claim 1, wherein said top wall of said shield includes a plurality of mounting apertures, said clip comprising a plurality of mounting projections extending from said base and secured in locked engagement in said mounting apertures of said shield.

5. The safety needle assembly of claim 1, wherein each said cannula finger lock includes a support leg extending from said base and a locking finger extending from said support leg, said locking finger being aligned and dimensioned for locked engagement with said needle cannula.

6. The safety needle assembly of claim 5, wherein the support leg is resiliently deflectable relative to said base.

7. The safety needle assembly of claim 6, wherein the locking finger of each said cannula finger lock is resiliently deflectable relative to said support leg.

8. The safety needle assembly of claim 5, wherein the locking finger of each said cannula finger lock is resiliently deflectable relative to said support leg.

9. The safety needle assembly of claim 3, wherein each said cannula finger lock is substantially rigid.

10. The safety needle assembly of claim 1, wherein said plurality of cannula finger locks define two cannula finger locks.

11. The safety needle assembly of claim 1, wherein said plurality of cannula finger locks define three cannula finger locks.

12. The safety needle assembly of claim 1, further comprising a medical device connected to said needle hub.

13. The safety needle assembly of claim 1, wherein the medical device comprises a holder for releasably receiving a fluid collection tube.

14. The safety needle assembly of claim 1, wherein the medical device is a syringe.

15. The safety needle assembly of claim 1, wherein the medical device comprises an intravenous infusion set.

* * * * *